United States Patent [19]

Preuss et al.

[11] 4,333,880
[45] Jun. 8, 1982

[54] 3-OXO-PREGNA-1,14,17-TRIEN-20-CAR-BOXYLATES AND PROCESS

[75] Inventors: Wolfgang Preuss, Monheim; Michael Bahn, Hilden; Rolf Schmid, Düsseldorf; Rüdiger Wagner, Monheim, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 228,177

[22] Filed: Jan. 26, 1981

[30] Foreign Application Priority Data

Feb. 4, 1980 [AT] Austria .................................. 582/80

[51] Int. Cl.³ ................................................. C07J 9/00
[52] U.S. Cl. ..................................... 260/397.1; 435/52
[58] Field of Search ........................ 260/397.1; 195/51

[56] References Cited

U.S. PATENT DOCUMENTS 3,994,933 11/1976 Jin et al. ........................... 260/397.1
4,252,730 2/1981 Krbechek ........................ 260/397.1

Primary Examiner—Elbert L. Roberts

Attorney, Agent, or Firm—Hammond & Littell, Weissenberger and Muserlian

[57] ABSTRACT

A $\Delta^{1,4,17}$-BNC compound having the formula:

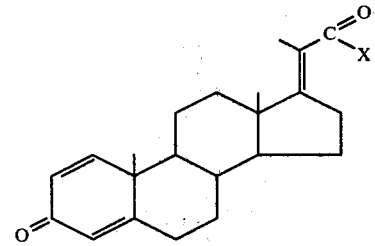

wherein X is a substituent selected from the group consisting of OH and OCH$_3$; as well as its process of production by microbiological side-chain splitting of a 17-C-side-chain steroid with a defect mutant microorganism which gives a steroid with a 17-C-α-propionic acid substituent in the absence of inhibitors inhibiting either the cleavage of the steroid ring or microorganism growth, where the defect mutant microorganisms are grown under a reduced air supply whereby an enrichment of $\Delta^{1,4,17}$-BNC occurs.

12 Claims, No Drawings

3-OXO-PREGNA-1,14,17-TRIEN-20-CARBOXYLATES AND PROCESS

BACKGROUND OF THE INVENTION

The subject matter of the published European patent application No. 0 004 913, corresponding to U.S. patent application Ser. No. 29,415, filed Apr. 12, 1979, is, among others, a process for the preparation of 17-C-steroid-α-propionic acid compounds, particularly for the preparation of 3-oxo-pregna-4-en-20-carboxylic acid ($\Delta^4$-BNC) and/or 3-oxo-pregna-1,4-dien-20-carboxylic acid ($\Delta^{1,4}$-BNC) by microbial side-chain splitting of 17-C-side-chain steroids. The process is characterized in that defect mutant microorganisms which give steroid compounds with the 17-C-α-propionic acid substituent even in the absence of inhibitors inhibiting either steroid ring cleavage and/or microorganism growth are grown in an aqueous nutrient medium under aerobic conditions in the presence of the steroid substrate with enrichment of the 17-C steroid-α-propionic acid compounds in the fermentation broth and $\Delta^4$-BNC and/or $\Delta^{1,4}$-BNC thus formed are isolated.

It is preferable to work with defect mutant microorganisms which have been grown by mutation and subsequent selection from previously selected wild strains which can grow on steroid compounds with 17-C-side chains as the preferable sole carbon source with an at least about equal splitting rate for the side chains as for the cleavage rate of the ring portion of the steroid compounds, but preferably an increased side-chain splitting rate. Particularly the block mutants from wild strains have been employed which, when grown on steroid compounds, yield a selective splitting under standard conditions according to the general formula:

$$I = a \cdot 10^b$$

where a denotes the growth factor and b the selectivity factor of the wild strain growth, and the selectivity index I of the wild strain is at least particularly $10^5$. The selectivity factor b of the wild strain used for growing the defect mutants should be at least 2, and the growth factor a preferably at least 0.2, particularly at least 1.

The growing of the wild strains of the subsequent selection according to their selectivity index I is effected on a 17-C-side-chain steroid as a carbon source of the type which is used as a starting material in decomposition methods, this steroid compound being preferably used as the sole carbon source for growing the wild strains.

The defect mutants preferably are strains which do not or practically do not grow on a mutant-separating medium in the growing of the mutant population from a known mutation of the selected wild strains, while the undesired accompanying mutant strains grow and were thus killed during their growth. Preferably block mutants of the genera Achromobacter, Arthrobacter, Bacillus, Brevibacterium, Corynebacterium, Flavobacterium, Microbacterium, Mycobacterium, Nocardia, Protaminobacterium, Serratia or Streptomyces are used.

The starting steroid compounds are those with saturated and/or unsaturated 17-C-side chains, where the side-chain radicals have preferably up to 10 carbon atoms, particularly 8 to 10 carbon atoms. Particularly suitable as starting materials are sterols of animal or vegetable origin, particularly cholesterol, sitosterol, stigmesterol, campesterol and/or ergosterol or their derivatives, such as cholestenone, sitostenone or stigmastenone.

Another embodiment of this process for the preparation of $\Delta^4$-BNC and $\Delta^{1,4}$-BNC is described in the published European patent application No. 0 015 308, which corresponds to U.S. patent application Ser. No. 128,223, filed Mar. 7, 1980. In this application defect mutants were used which were obtained, however, from a wild strain which supplies, at least partly, 17-C-steroid-α-propionic acid compounds in the aerobic growth on sterol compounds in the presence of inhibitors for the enzymatic ring cleavage of the sterol compounds. In particular, those wild strains were isolated and grown which show, in the growth on sterol compounds with saturated or unsaturated alkyl radicals on the 17-C with 8 to 10 carbon atoms, a yield of 17-C-steroid-α-propionic acid compounds, measured under standard conditions, of at least 5% by weight, preferably at least 10% by weight, related to the sterol compounds used.

Preferably wild strains of microorganisms are isolated and grown, which when grown on sterol compounds of the above-mentioned type yield a selective splitting according to the general formula:

$$I = a \cdot 10^p$$

where a denotes the growth factor and p the selective factor of the wild strain growth, and the selectivity index I has a numerical value of at least 1, preferably at least 2, and particularly at least 20. The growth factor a of the wild strain should be at least 0.2 under standard conditions, preferably at least 1, and the selectivity factor p under standard conditions at least 0.5, preferably at least 1. The preferred wild strains for the subsequent production of the defect mutants should prefer the 17-C-side-chain splitting over the ring cleavage. The mutation treatment of the wild strains is effected under such conditions of concentration and a duration of action of the mutagenic agent that 10% to 99.999% of the starting population of the microorganisms are inactivated by the mutagenic treatment, working preferably with a killing rate of 90% to 99.99%.

$\Delta^4$-BNC has the structural formula:

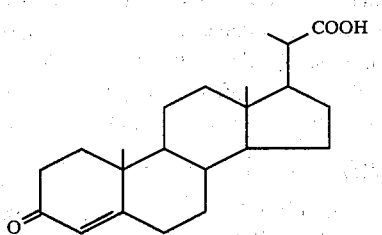

and $\Delta^{1,4}$-BNC has the structural formula:

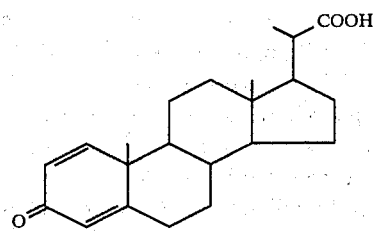

FIAT final report No. 996 (1947), pages 24–26, describes a chemical modification of phytosterol acetate to progesterone by means of a modified Curtius degradation.

Julian et al, J. Am. Chem. Soc. 70, pp. 887–892 (1948), describes 3-acetoxy-5-bisnor-cholenic acid (BNC) and its conversion to Δ20-pregnenes by a Curtius procedure.

Moersch et al, J. Org. Chem. 29, pp. 2495–2499 (1964), describe the production of 3-halo-androsta-1,3,5-trienes from androsta-1,4-dien-3-ones.

OBJECTS OF THE INVENTION

An object of the present invention is the obtaining of a Δ1,4,17-BNC compound having the formula:

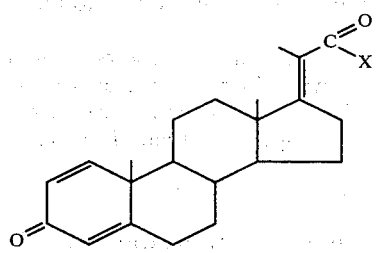

where X is a substituent selected from the group consisting of OH and OCH3.

Another object of the present invention is the development of an improvement in the process for the production of the above Δ1,4,17-BNC compound comprising cultivating a defect mutant microorganism which gives a steroid with a 17-C-α-propionic acid substituent in the absence of inhibitors inhibiting either the cleavage of a steroid ring or microorganism growth, in an aqueous nutrient medium under aerobic conditions containing a 17-C-side-chain steroid having more than 3 carbon atoms in the side chain as a carbon source, and recovering said Δ1,4,17-BNC-compound, the improvement consisting of conducting said aerobic cultivation under conditions of a reduced air supply sufficient to cause an enrichment of Δ1,4,17-BNC compounds.

These and other objects of the invention will become more apparent as the description thereof proceeds.

DESCRIPTION OF THE INVENTION

We have now found that the decomposition product, 20-carboxy-pregna-1,4,17(20)-trien-3-one, hereafter called Δ1,4,17-BNC, which has not been described before, can be obtained in the fermentation of sterol compounds with defect mutant microorganism according to the teaching of the European patent application Nos. 0 004 913 and 0 015 308, corresponding, respectively, to commonly assigned U.S. patent applications Ser. No. 29,415, filed Apr. 12, 1979, and Ser. No. 128,223, filed Mar. 7, 1980, incorporated herein by reference.

The structural formula of Δ1,4,17-BNC is the following:

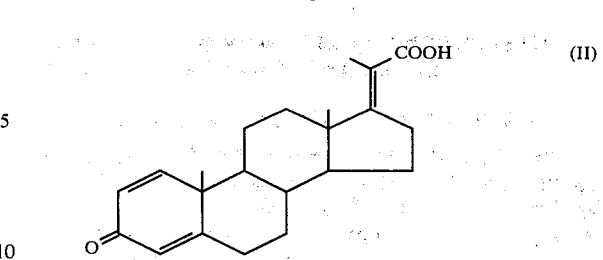

The subject of the present invention is accordingly in a first embodiment the new compound Δ1,4,17-BNC, as well as the corresponding methyl ester of this new compound. This derivative has likewise never been described before.

The new compounds of the invention correspond to the general formula (I)

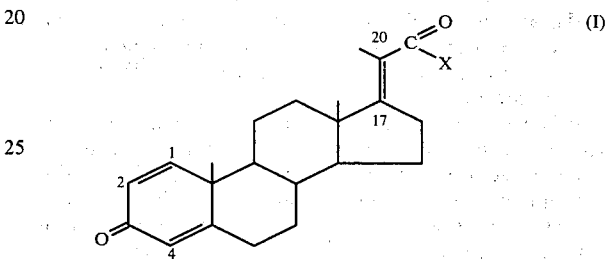

wherein X represents the radical OH or OCH3. The methyl ester can be obtained from Δ1,4,17-BNC by conventional esterification as will be described later.

The invention concerns furthermore an improvement in the process for the preparation of 20-carboxy-pregna-1,4,17-(20)-trien-3-one (Δ1,4,17-BNC) by microbial side-chain splitting of 17-C-side-chain steroid substrates in an aqueous nutrient medium under aerobic conditions with defect mutant microorganisms, which supply steroid compounds with the 17-C-α-propionic acid substituent even in the absence of inhibitors inhibiting the cleavage of the steroid ring and/or inhibiting the growth characterized in that the defect mutant microorganisms are grown under a reduced air supply whereby an enrichment of Δ1,4,17-BNC is obtained in the product mix, and the latter is isolated from the reaction product.

For details of the production of the defect mutant microorganisms, see the data in the published European patent application Nos. 0 004 913 and 0 015 308. In the further development of the methods for the decomposition of sterol with these defect mutant microorganisms, it was found that by reducing the air supply during the fermentation, Δ1,4,17-BNC, which has not been described before, can be obtained in such higher yields that their technical production becomes of interest.

By varying the oxygen deficit in the fermenter liquid, the yield of the desired Δ1,4,17-BNC can be influenced. The optimum working conditions regarding the oxygen deficit depend on the strain and can be determined from case to case by preliminary tests. In general, a saturation of oxygen in the fermenter liquid phase of not more than about 90% pO2 is preferred, where 100% pO2 is the partial pressure of the oxygen dissolved in the fermenter liquid phase under the working conditions with unlimited supply of air or oxygen.

According to the invention, it is furthermore preferred to work with corresponding saturation concentrations of oxygen in the fermenter liquid phase in the range of from 30% to 70% $pO^2$. The adjustment and maintenance of predetermined saturation concentrations by reducing the supply of oxygen is possible according to the method of the invention without great difficulties. The defect mutant microorganisms used according to the invention grow relatively slowly, which facilitates the control of oxygen dissolved in the fermenter liquid phase.

When cultivating with a number of defect mutant microorganisms, as used according to the invention, the reducing of the air supply leads to a limited reduction of the total yield of BNC-type compounds compared to a method with unlimited air supply. The BNC-type compounds which are or can be formed when working with the mutant strains in question are primarily $\Delta^4$-BNC and $\Delta^{1,4}$-BNC, described in the above-mentioned European patent applications, as well as $\Delta^{1,4,17(20)}$-BNC to a lesser extent.

When working with mutant strains where the reduction of the air supply leads to a reduction of the total yield, it may be advisable to fix the extent of the reduction of the yield to at least 5%, preferably to at least 10%, compared with the standard yield with unlimited air supply. It may even be advisable to work with even greater limitations of the yield, so that the reduction of the total yield of BNC-type compounds per unit of time under otherwise comparable conditions is 30%, 40% or even 50%. The yield of $\Delta^{1,4,17}$-BNC rises related to the total reaction products obtained.

It was also found that a number of selected defect mutants are capable of forming increased amounts of $\Delta^{1,4,17}$-BNC, regardless of the regulation of the air supply. But here too, the yield of desired products can be further increased by reducing the air supply during fermentation. Particularly suitable are secondary strains of the strain deposited in the German Collection for Microorganisms (DMS) in Göttingen, Germany, with the internal designation T 191, deposition No. DSM 1444. The deposition numbers of the defect mutants used within the framework of the invention are the following: ATCC 31636 and DSM 1990.

It was also found expedient to use at least partly water-miscible solvents for the starting steroid substrate in order to increase the yield of $\Delta^{1,4,17}$-BNC in the fermenter. In particular, it may be advisable to use solvents which are completely water miscible. The steroid substrate is preferably dissolved in the water-miscible solvent and is introduced in this form into the fermenter. The water-miscible solvents of the type described are organic solvents. Examples are alcohols, particularly water-miscible lower alkanols, such as methanol or ethanol; dimethyl-formamide, dioxane, tetrahydrofuran or dimethyl sulfoxide. The transformation of the sterol substrate to $\Delta^{1,4,17}$-BNC can be effected this way not only with improved yields, but additionally with a considerable acceleration of the reaction.

The water-miscible organic solvents are preferably used in a multiple amount by weight, related to the steroid substrate charged. Preferred are mixing ratios of steroid substance/solvent in the range of 1 part by weight: 5 to 100 parts by weight. Mixing ratios of 1:10 to 30 parts by weight are particularly preferred.

For details of the incubation process, see the data in the published European patent application No. 0 004 913, corresponding to U.S. Ser. No. 29,415, both incorporated herein by reference. Particularly suitable as starting steroid compounds are those with a saturated and/or unsaturated 17-C-side chain with preferably up to 10 carbon atoms, particularly 8 to 10 carbon atoms. Preferred, as starting materials, are sterols of animal or vegetable origin. Particularly suitable starting materials are chlorestero, sitosterol, stigmasterol, campesterol and/or ergosterol, as well as their derivatives, such as cholestenone, sitostenone or stigmastenone.

The steroid compound used as a starting material can be added to the culture during the incubation period or it can be added to the nutrient medium before the inoculation with the defect mutant inoculum. It is possible to use a single steroid compound or a mixture of several steroid compounds. Preferably the steroid compounds to be split selectively are used in the culture media in amounts of about 0.1 to 100 gm/liter. The optimum concentration of the sterol compound to be transformed in the growth stage generally depends on the strain and can be determined in each case by simple preliminary tests. In general, the concentration of the sterol compound in the medium preferably is not over 30 gm/liter, and frequently not over 20 gm/liter.

It may be advisable to add the steroid substrate to be subjected to the side-chain splitting not at once to the reaction mixture, but gradually in the course of the reaction. Preferably the starting steroid substrate is added in this embodiment substantially continuously to the reaction mixture in the course of the splitting reaction. This way the yield of the desired decomposition products can be frequently increased.

The culture is grown in a nutrient medium which contains as a carbon source either the sterols to be transformed or additional metabolizable carbon sources, as well as the nutrient and growth substances generally required by these microorganisms.

Particularly favorable for the growth of the microorganisms are, for example, paraffin, glycerine, carboxylic acids, starch, dextrin, saccharose, glucose, fructose and sugar-containing waste products. Suitable nitrogen sources are ammonium salts, nitrates, peptone, corn-steeped liquor, zein, soy flour, distillers' waste and fish meal. Fermentation accelerators, such as yeast extracts and vitamins, can also be added. The nutrient medium contains, in addition, preferably inorganic salts, such as sodium, potassium, or ammonium phosphates, as well as calcium, magnesium, manganese or iron salts. The emulsification of the sterols in the nutrient medium is preferably effected by means of known emulsifiers, for example, by means of fatty acid-sorbitan esters or their ethylene oxide adducts, such as the Tweens, polyoxyethylene-monolauryl ether, or fatty acid-amide alkyl-betaine.

The culture medium used is sterilized before the start of the bacterial culture, preferably by heating. After cooling and inoculation of the culture medium with a suitable preliminary culture of the bacterial strain, it is incubated between 25° and 35° C., preferably 27° C. to 30° C. The pH value of the nutrient solution is adjusted between 4 and 8.5, preferably between 7.0 and 8.0. The culture is supplied to the desired extent with oxygen by shaking, stirring or by the introduction of gas, and incubated until the sterols are split to the desired stage. The decomposition of the sterols takes as a rule 24 to 160 hours, depending on the substrate concentration and other fermentation conditions. It was found that the desired $\Delta^{1,4,17}$-BNC frequently attains the desired yield optimum faster than other accompanying BNC compounds. In this event, it may be advisable according to the invention not to attempt a total reaction of the sterol starting material but to isolate the product by shortening the incubation period when the desired yield of $\Delta^{1,4,17}$-BNC has been obtained.

The product obtained this way, which is usually enriched in the fermentation booth, can then be obtained in known manner from the reaction mixture. Thus, for example, the BNC compounds can be isolated from the culture medium before or after the separation of the cells by extraction with organic solvents, like methylene chloride, methylisobutyl ketone, ethyl acetate, n-hexanol, n-octanol, chloroform or n-hexane.

According to a preferred embodiment, the reaction product can be simply isolated from the fermentater liquid by precipitation in the acid range and filtration. To this end the alkaline fermenter liquid is first filtered to remove the cell material and other solid components, then it is acidified. The product precipitated in solid filterable form can be obtained, for example, by a simple vacuum filtration. The reaction product is then worked up, whereby $\Delta^{1,4,17}$-BNC is obtained in pure form. The precipitated solid consists almost exclusively of a mixture of $\Delta^{1,4,17}$-BNC, $\Delta^{1,4}$-BNC (20-carboxy-pregna-1,4-dien-3-one), and $\Delta^4$-BNC (20-carboxy-pregna-4-en-3-one). The working up of this product mixture is effected, for example, by chromatographic methods in the form of the free acid or after esterification in the form of the methyl ester.

Conversion of the free acid to the methyl ester is possible in known manner by reaction with diazomethane. The reaction itself takes place in a manner known from the literature.

$\Delta^{1,4,17}$-BNC is an important intermediate product for the partial synthesis of pharmaceutically effective steroids. A particular advantage of its use over $\Delta^{1,4}$-BNC or $\Delta^4$-BNC is the presence of the additional 17(20)-double bond, which permits or facilitates the frequently desired introduction of a substituent on the 17 carbon atom.

U.S. Pat. No. 3,994,933 describes 20-carboxy-pregna-4,17(20)-dien-3-one and its preparation by microbial decomposition from sterols. This known compound differs from the compound according to the present invention by the absence of the $\Delta^1$-double bond. The presence of this double bond can be a considerable advantage over the known compound in the use as an intermediate pharmaceutical product.

The following examples are illustrative of the practice of the invention without being limitative in any manner.

EXAMPLES

The percentages in the following examples are percent by weight unless otherwise stated.

EXAMPLE 1

The defect mutant microorganisms indicated below were grown aerobically in 500 ml Erlenmeyer flasks with 100 ml of nutrient solution of the following compositions:

| Percent By Weight | |
|---|---|
| 0.5 | Peptone |
| 0.8 | Yeast extract |
| 0.4 | Zein |
| 0.3 | Glucose |
| 0.05 | Tween 80 (polyoxyethylene sorbitan monooleate) |
| 0.05 | Cholesterol, pH 7.2. |

The culture was preincubated on the shaking machine (shaking frequency 150 rpm) at 30° C. for 48 hours. Then 0.2% of emulsifier and 0.1% of cholesterol were added and incubated for a further 120 hours. After stopping the fermentation, samples were taken, standardized to pH 2.0, extracted 1:1 with ethyl acetate and analyzed by thin layer chromatography. The yields of the various strains are indicated in the following Table I.

In order to obtain lower air saturation values in the reaction medium in these tests, we used, instead of the shaking flasks from the known state of the art with four baffles (indentations or depressions in the glass wall close to the bottom of about 2 cm length and 1 cm depth), baffle-free shaking flasks.

The compounds were identified by high performance-thin layer chromatography.

The results with the various methods are as follows:

TABLE I

| Internal Number | Deposition Number | Conditions | $\Delta^{1,4}$-BNC mg/100 ml | $\Delta^{1,4,17}$-BNC mg/100 ml |
|---|---|---|---|---|
| T 191 | DSM 1444 | According to Example 3 published European patent application 0 004 913 | 80 | 12 |
| T 191-1091 | ATCC 31636 | As above | 95 | 19 |
| T 191-1091 | | As above, but with baffle-free flasks | 34 | 10 |

EXAMPLE 2

The free $\Delta^{1,4,17}$-BNC was converted with diazomethane to its methyl ester after isolation from the reaction mixture, and subjected in this form to purification by preparative high pressure liquid chromatography. The conditions, as well as the spectroscopic data of the methyl ester purified this way, are indicated below:

| Conditions for the high pressure liquid chromatography: | |
|---|---|
| Column: | Silica gel column by DuPont, filled with Zorbox SIL, mean particle size 7 μ |
| Length: | 250 mm |
| Inside diameter: | 23 mm |
| Elution agent: | Isooctane/isopropanol (98:2) |
| Conditions: | 50 ml/min (flow through) 50 bar 298$^K$ |
| Detection: | UV-detector, 254 nm. |

Spectroscopic data of the methyl ester of $\Delta^{1,4,17}$-BNC (1) IR-spectrum (CHCl$_3$): 1714 cm$^{-1}$ (C=O, ester); 1660 cm$^{-1}$ (C=O, ketone); 1625 cm$^{-1}$; 1603 cm$^{-1}$.

(2) $^1$H-NMR-spectrum (80 MHz, CDCl$_3$, δ-values): 18-CH$_3$: 0.99 ppm s; 19-CH$_3$: 1.24 ppm s; 21-CH$_3$: 1.93 ppm t (J=1.9 Hz); 0-CH$_3$: 3.69 ppm s.

Olefinic protons: ABC-system with lines at: 6.07; 6.12; 6.15; 6.27; 6.30; 6.97; 7.10 ppm.

The remaining protons (methylene and methine protons) supply signals in the expected range.

(3) $^{13}$C-NMR, broad band-noise decoupled and off resonance (20 MHz, CDCl$_3$, TMS as standard).

| | |
|---|---|
| C-18, C-19, C-21: | 14.6 ppm q |
| | 15.5 ppm q |
| | 18.7 ppm q |
| O—CH$_3$: | 51.1 ppm q |
| C-1: | 155.5 ppm d |
| C-2: | 127.7 ppm d |
| C-3: | 186.2 ppm s |
| C-4: | 124.0 ppm d |
| C-5: | 168.6 ppm s |
| C-22: | 162.8 ppm s |
| C-17: | 155.3 ppm s |
| C-20: | 118.6 ppm s |
| Other signals at: | 23.1; 24.8; 32.7; 33.5; 35.0; 36.5; 43.4; 46.9; 51.9; 54.6; 55.1 ppm. |

(4) UV-spectrum λ max. (isopropanol): 239 nm.
(5) Mass spectrum: M+ 354 nm.
Other Data: Melting point: 155° C. to 161° C.

EXAMPLE 3

Example 1 was repeated under the conditions indicated there, but instead of cholesterol, a mixture of vegetable sterol compounds obtained from soybean oil was used as a steroid substrate. The composition of this vegetable sterol was as follows: total content of sterol compound about 88% by weight (56% by weight sitosterol, 28% by weight campesterol, and 4% by weight of stigmasterol), sterol hydrocarbons and cholesterol 4% to 6% by weight, triterpene alcohols, testosteroids and other steroid components 4% to 6%.

The culture of strains T 191 (DSM 1444) and T 191-1091 (ATCC 31636) was preincubated on the shaking machine (shaking frequency 150 rpm) at 30° C. for 48 hours, then 0.2% by weight of emulsifier and 0.5% of the vegetable sterol were added, and the incubation was continued for another 120 hours. After the fermentation had stopped, samples were taken, standardized to pH 2.0, extracted 1:1 with ethyl acetate and analyzed by thin-layer chromatography. The yields obtained are practically identical with the comparable values of Example 1.

EXAMPLE 4

The defect mutant strain SC 372-837 (DSM 1990) is capable of forming increased amounts of Δ$^{1,4,17}$-BNC from the vegetable sterol of Example 3, or allows the shortening of the duration of the preliminary incubation by half compared to Example 3.

Strain SC 372-837 was grown aerobically in 500 ml Erlenmeyer flasks with 100 ml nutrient solution of the following composition:
0.5%: Peptone
0.8%: Yeast extract
0.4%: Zein
0.3%: Glucose
0.05%: Emulsifier
0.05%: Vegetable sterol, pH 7.2.

The culture was preincubated on the shaking machine (shaking frequency 150 rpm) at 30° C. for 24 hours, then 0.2% of emulsifier and 0.5% of vegetable sterol were added, and the incubation was continued for another 120 hours. After the fermentation had stopped, samples were taken, standardized to pH 2.0, extracted 1:1 with ethyl acetate, and analyzed by thin-layer chromatography.

Δ$^{1,4}$-BNC yield: 49 mg/100 ml
Δ$^{1,4,17}$-BNC yield: 15 mg/100 ml.

EXAMPLE 5

DSM 1444 was used in Examples 5 to 7 as the defect mutant microorganism strain. The defect mutants were grown aerobically in a 1.5 liter fermenter containing a 1 liter nutrient solution of the following composition:
0.05%: Peptone
0.8%: Yeast estract
0.4%: Zein
0.3%: Glucose
0.05%: Emulsifier
0.1%: Cholesterol at pH 7.2.

The culture was preincubated for 24 hours at 30° C. at 700 rpm stirrer speed and injection of 1.0 VVM (VVM=volume air/volume liquid phase/minute), subsequently 0.2% of emulsifier and 0.4% of cholesterol were added and the medium was fermented for another 100 hours.

After the fermentation was stopped, samples were taken, standardized to pH 2.0, extracted 1:1 with ethyl acetate and analyzed by thin-layer chromatography.

The yields are compiled after Example 12 in Table II.

EXAMPLE 6

The defect mutants were grown in a 1.5 liter fermenter with 1 liter nutrient solution of the following composition:
0.05%: Peptone
0.8%: Yeast extract
0.4%: Zein
0.3%: Glucose
0.05%: Emulsifier
0.1%: Cholesterol at pH 7.2.

The culture was preincubated at 30° C., 700 rpm and 0.5 VVM for 24 hours. Subsequently 0.2% of emulsifier and 0.4% of cholesterol were added and the medium was fermented for another 100 hours.

After the fermentation was stopped, samples were taken, standardized to pH 2.0, extracted 1:1 with ethyl acetate and analyzed by thin-layer chromatography.

The yields are compiled after Example 12 in Table II.

EXAMPLE 7

The defect mutants were grown aerobically in a 1.5 liter fermenter with 1 liter nutrient solution of the following composition:
0.05%: Peptone
0.8%: Yeast extract
0.4%: Zein
0.3%: Glucose
0.05%: Emulsifier
0.1%: Cholesterol at pH 7.2.

The culture was preincubated at 30° C., 700 rpm and 0.2 VVM for 24 hours. Subsequently 0.2% of emulsifier and 0.4% of cholesterol were added and the medium was fermented for another 100 hours.

After the fermentation was stopped, samples were taken, standardized to pH 2.0, extracted 1:1 with ethyl acetate and analyzed by thin-layer chromatography.

The yields are compiled after Example 12 in Table II.

EXAMPLE 8

SC 372-837 (DSM 1990) were used in Examples 8 to 12 as defect mutant microorganism strain. The defect mutants were grown aerobically in a 1.5 liter fermenter with 1 liter nutrient solution of the following composition:

3.0%: Tryptone soy broth
0.1%: NH$_4$NO$_3$
0.6%: Yeast extract
0.05%: myo Inosit
0.15%: Lactic acid
0.15%: Succinic acid
0.1%: Emulsifier at pH 7.2.

The culture were preincubated at 30° C., 700 rpm and 1.0 VVM for 24 hours. Subsequently 0.1% of emulsifier and 0.5% of vegetable sterol were added, and the medium was fermented for another 100 hours.

After the fermentation was stopped, samples were taken, standardized to pH 2.0, extracted 1:1 with ethyl acetate, and analyzed by thin-layer chromatography.

The yields are compiled after Example 12 in Table II.

EXAMPLE 9

The defect mutants were grown aerobically in a 1.5 liter fermenter with 1 liter nutrient solution of the following composition:

3.0%: Tryptone soy broth
0.1%: NH$_4$NO$_3$
0.6%: Yeast extract
0.05%: myo Inosit
0.15%: Lactic acid
0.15%: Succinic acid
0.1%: Emulsifier at pH 72.

The culture was preincubated at 30° C., 700 rpm and 0.2 VVM for 24 hours. Subsequently 0.1% of emulsifier (Tween 80) and 0.5% of vegetable sterol were added and the medium was fermented for another 100 hours.

After the fermentation was stopped, samples were taken, standardized to pH 2.0, extracted 1:1 with ethyl acetate, and analyzed by thin-layer chromatography.

The yields are compiled after Example 12 in Table II.

EXAMPLE 10

The defect mutants were grown aerobically in a 1.5 liter fermenter with 1 liter nutrient solution of the following composition:

3.0%: Tryptone soy broth
0.1%: NH$_4$NO$_3$
0.6%: Yeast extract
0.05%: myo Inosit
0.15%: Lactic acid
0.15%: Succinic acid
0.1%: Emulsifier at pH 7.2.

The culture was preincubated at 30° C., 700 rpm and 0.5 VVM for 24 hours. Subsequently 0.1% of emulsifier and 0.5% of vegetable sterol were added and the medium was fermented for another 24 hours.

After the fermentation was stopped, samples were taken, standardized to pH 2.0, extracted 1:1 with ethyl acetate and analyzed by thin-layer chromatography.

The yields are compiled after Example 12 in Table II.

EXAMPLE 11

The defect mutants were grown aerobically in a 1.5 liter fermenter with 1 liter nutrient solution of the following composition:

3.0%: Tryptone soy broth
0.1%: NH$_4$NO$_3$
0.6%: Yeast extract
0.05%: myo Inosit
0.15%: Lactic acid
0.15%: Succinic acid
0.1%: Emulsifier at pH 7.2.

The culture was preincubated at 30° C., 700 rpm and 1 VVM for 24 hours. Subsequently 0.1% of emulsifier, 3% of dimethyl formamide and 0.5% of vegetable sterol were added and the medium was fermented for another 24 hours.

After the fermentation was stopped, samples were taken, standardized to pH 2.0, extracted 1:1 with ethyl acetate and analyzed by thin-layer chromatography.

The yields are compiled after Example 12 in Table II.

EXAMPLE 12

The defect mutants were grown aerobically in a 1.5 liter fermenter with 1 liter nutrient solution of the following composition:

3.0%: Tryptone soy broth
0.1%: NH$_4$NO$_3$
0.6%: Yeast extract
0.05%: myo Inosit
0.15%: Lactic acid
0.15%: Succinic acid
0.1%: Emulsifier at pH 7.2.

The culture was preincubated at 30° C., 700 rpm and 1 VVM for 24 hours. Subsequently 0.1% of emulsifier, 3% of dimethyl formamide and 0.5% of vegetable sterol were added and the medium was fermented for another 100 hours.

After the fermentation was stopped, samples were taken, standardized to pH 2.0, extracted 1:1 with ethyl acetate, and analyzed by thin-layer chromatography.

The yields are compiled in Table II.

TABLE II

| Internal No. | Deposition No. | Example | $\Delta^{1,4}$-BNC mg/100 ml | $\Delta^{1,4,17}$-BNC mg/100 ml | pO$_2$ % |
|---|---|---|---|---|---|
| T 191 | DSM 1444 | 5 | 350 | 40 | 100 |
| | | 6 | 200 | 75 | 70 |
| | | 7 | 150 | 65 | 30 |
| SC 372-837 | DSM 1990 | 8 | 66 | 10 | 100 |
| | | 9 | 60 | 25 | 30 |
| | | 10 | 37 | 35 | 65 |
| | | 11 | 71 | 36 | 100 |
| | | 12 | 95 | 46 | 100 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A $\Delta^{1,4,17}$-BNC compound having the formula:

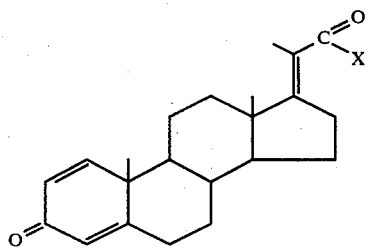

wherein X is a substituent selected from the group consisting of OH and OCH$_3$.

2. The $\Delta^{1,4,17}$-BNC compound of claim 1 wherein R is OH

3. The $\Delta^{1,4,17}$-BNC compound of claim 1 wherein R is OCH$_3$.

4. In the process for the production of the $\Delta^{1,4,17}$-BNC compound of claim 1 comprising cultivating a defect mutant microorganism which gives a steroid with a 17-C-α-propionic acid substituent in the absence of inhibitors inhibiting either the cleavage of a steroid ring or microorganism growth, in an aqueous nutrient medium under aerobic conditions containing a 17-C-side-chain steroid having more than 3 carbon atoms in the side chain as a carbon source, and recovering said $\Delta^{1,4,17}$-BNC compound, the improvement consisting of conducting said aerobic cultivation under conditions of a reduced air supply sufficient to cause an enrichment of $\Delta^{1,14,17}$-BNC compounds.

5. The process of claim 4 wherein the saturation concentration of oxygen in said aqueous nutrient medium does not exceed 90%.

6. The process of claim 5 wherein the saturation concentration of oxygen in said aqueous nutrient medium is maintained between 30% and 70%.

7. The process of claim 4 wherein said air supply is reduced sufficiently so that the total amount of BNC compounds produced by said cultivation is reduced at least 5% by weight, as compared to said cultivation with an unlimited air supply.

8. The process of claim 4 wherein said air supply is reduced sufficiently so that the total amount of BNC compounds produced by said cultivation is reduced at least 10% by weight, as compared to said cultivation with an unlimited air supply.

9. The process of claim 4 or 5 or 6 or 7 or 8 wherein said cultivating is conducted in the presence of at least partly water-miscible organic solvents capable of dissolving said 17-C-side-chain steroid.

10. The process of claim 4 or 5 or 6 or 7 or 8 wherein said cultivating is conducted in the presence of a completely water-miscible organic solvent capable of dissolving said 17-C-side-chain steroid.

11. The process of claim 4 or 5 or 6 or 7 or 8 or 9 wherein said 17-C-side-chain steroid having more than 3 carbon atoms is a steroid having from 3 to 10 carbon atoms in the 17-C-side chain of animal or vegetable origin.

12. The process of claim 4 wherein said defect mutant microorganism is that deposited under the depository number DSM 1444.

* * * * *